(12) United States Patent
Danger

(10) Patent No.: US 6,179,616 B1
(45) Date of Patent: Jan. 30, 2001

(54) DENTAL DRILL

(75) Inventor: Karl-Heinz Danger, Detmold (DE)

(73) Assignee: Gebr. Brasseler GmbH & Co. KG, Lemgo (DE)

( * ) Notice: Under 35 U.S.C. 154(b), the term of this patent shall be extended for 0 days.

(21) Appl. No.: 09/300,469

(22) Filed: Apr. 28, 1999

(30) Foreign Application Priority Data

May 27, 1998 (DE) ............................................. 198 23 720

(51) Int. Cl.$^7$ ........................................................ A61C 3/02
(52) U.S. Cl. ................................................................. 433/165
(58) Field of Search ................................. 433/165, 166, 433/102; D24/146; 408/223, 224, 230; 407/57, 58, 59

(56) References Cited

U.S. PATENT DOCUMENTS

| | | | |
|---|---|---|---|
| 3,443,459 | * | 5/1969 | Mackey et al. ........................ 408/230 |
| 4,284,406 | * | 8/1981 | Hughes ................................. 433/165 |
| 4,285,618 | * | 8/1981 | Shanley, Jr. ............................ 407/54 |
| 4,990,035 | * | 2/1991 | Scheuch et al. ........................ 407/30 |
| 5,236,357 | * | 8/1993 | Randin ................................. 433/102 |
| 5,575,650 | * | 11/1996 | Niznick et al. ....................... 433/165 |
| 5,725,338 | * | 3/1998 | Cabaret et al. ....................... 408/230 |

FOREIGN PATENT DOCUMENTS

19602030 * 7/1997 (DE) .

OTHER PUBLICATIONS

Busch & Co. Catalogue—p. 5, published prior to Apr. 28, 1999.*
Busch & Co. Catalogue—p. 10, published prior to Apr. 28, 1999.*
Busch & Co. Catalogue—p. unknown, published prior to Apr. 28, 1999.*

* cited by examiner

Primary Examiner—John J. Wilson
Assistant Examiner—Melba Bumgarner
(74) Attorney, Agent, or Firm—Shinjyu Global IP Counselors, LLP

(57) ABSTRACT

The present invention relates to a dental drill comprising a shaft (2) and a cutting portion (3) provided with cutting edges. At the front side, the dental drill (1) comprises two main cutting edges (5) and, laterally on the cutting portion, a plurality of additional cutting edges (7). The main cutting edges (5) converge in a central axis of the dental drill and directly pass into two lateral cutting edges (8).

9 Claims, 2 Drawing Sheets

DENTAL DRILL

BACKGROUND OF THE INVENTION

1. Field of the Invention

This invention generally relates to a dental drill. More specifically, the present invention relates to a dental drill having a shaft and a cutting portion with cutting edges.

2. Background Information

In the dental field, drills are commonly used, among other things, for drilling out fillings in teeth. In many cases the fillings consist of amalgam which contains a high amount of mercury. When such fillings are drilled out, minute mercury-containing particles or pieces are formed. These minute mercury-containing particles or pieces may be swallowed by the patient, as well as mercury vapors which may be inhaled by the patient and/or the dentist, possibly resulting in mercury poisoning. Hence, in the case of conventionally used drills, there exists a risk that patients and dentists might be exposed to a high mercury load.

Moreover, as for dental preparatory techniques, it is important that as little as possible of the healthy tooth material be removed while the fillings are being drilled. As a result, the tooth is just damaged to the necessary degree on the one hand and the subsequent treatment of the tooth is facilitated on the other hand, since the existing healthy tooth material remains to a maximum degree.

German Publication DE 195 02 030 A1 already discloses a drill for metal working in which two main cutting edges are provided at the front side converge in the central axis and pass into two secondary cutting edges of a cutting portion on their radially outer end portions. The cutting portion does not comprise any additional cutting edges.

In view of the above, there exists a need for a dental drill which overcomes the above mentioned problems in the prior art. This invention addresses this need in the prior art as well as other needs, which will become apparent to those skilled in the art from this disclosure.

SUMMARY OF THE INVENTION

It is the object of the present invention to provide a dental drill which while having a simple structure and being easy to handle can be produced at low costs and permits a rapid drilling of fillings with little strain on the patient.

According to the invention this object is achieved through the features of the main claim. The subclaims show advantageous developments of the invention.

Hence, according to the invention a dental drill is provided with a shaft and a cutting portion equipped with cutting edges. At the front side the dental drill comprises two main cutting edges and a transitional cutting edge. Several additional cutting edges are arranged laterally on the cutting portion or head. The main cutting edges of the dental drill converge in a central axis of the dental drill and directly pass into two lateral cutting edges. In an advantageous embodiment the main cutting edges form a tip or a transitional cutting edge which is semicircular when viewed laterally.

The dental drill of the invention is characterized by a number of considerable advantages. Due to the fact that the two main cutting edges are arranged at the front area of the cutting portion, the drilling performance of the dental drill in the axial direction is excellent. Since the two main cutting edges are advantageously configured such that they converge and meet at the central axis of the dental drill, the drill cuts across the whole area of the main cutting edge. This means that the inventive drill need not comprise any transverse cutting edge. As a consequence, the disadvantageous effect of the transverse cutting edge, which normally interconnects the, two main cutting edges and only squeezes the material to be drilled in the area of the transverse cutting edge can be avoided. As a result, the dental drill exhibits excellent cutting effects and fillings can be drilled out very rapidly. Since at least two additional cutting edges into which the two main cutting edges directly extend are provided laterally on the cutting portion, a dentist can also remove filling material by preparatory techniques exploiting lateral contact. Hence, the dentist in sectioning the filling can produce relatively large pieces of material, which can then be sucked off from the patient's mouth in an easy and reliable manner e.g. by means of a suction device or can be removed from the mouth by rinsing the same. The risk that drilled filling material will be swallowed by the patient can thus be considerably reduced.

The lateral cutting edges are advantageously arranged along helical lines. As a result, the lateral cutting portion can be produced relatively easily and an adequate transverse cutting force is imparted to the drill to remove material in a time saving manner by way of a preparatory technique exploiting lateral contact. Such an arrangement also helps to suppress vibrations and the occurrence of drilling noise.

Advantageously, the lateral cutting edges comprise radial incisions. As a result, the friction on the lateral area of the drill is reduced, resulting in less frictional heat and thus a smaller amount of mercury vapor. Hence, in particular in amalgam fillings the mercury load on the patient and the dentist due to mercury vapors can be minimized. The production of frictional forces can be influenced at the lateral cutting edges by identical or different distances of the individual sections and can thus be optimized in a simple manner for the respective demands, e.g. different depths or sizes of the fillings.

To keep the amount of heat produced by the lateral cutting edges as small as possible, the incisions are arranged on the lateral cutting edges relative to a line perpendicular to the central axis at an angle ranging from 5° to 15°. Hence, the incisions of the individual lateral cutting edges are arranged in offset fashion in the longitudinal direction of the dental drill.

In a preferred embodiment the dental drill comprises four lateral cutting edges and four helical grooves. As a result, the production of relatively large pieces of material can be ensured while fillings are being drilled. At the same time, a high removal rate is achieved, so that a filling can be drilled out within a short period of time. This saves time during treatment and also shortens inconvenient situations for the patient, e.g. the mouth need no longer be kept open for long periods of time. Hence, optimum cutting parameters and minimum strain on the patient can be achieved.

Hence, the use of the drill according to the invention results, in particular, in economic advantages due to a shorter treatment time and a longer service life.

To ensure a high cutting performance, the lateral cutting edges are shaped as a staggered or diamond toothing according to a further embodiment of the invention. During the drilling operation relatively large pieces of the filling are thereby produced and the occurrence of mercury vapors is minimized. Technical preparatory work by lateral contact in virtually all positions of the drill relative to the tooth or filling is also made possible thereby. Hence, such a drill is particularly suited for drilling fillings in mouth areas, which are difficult to reach.

Depending on the intended use, the main cutting edges are straight or curved. Thus, different advantageous geometries can be ensured for the cutting portion and, in particular, for the front side of the cutting portion. Depending on the intended use or type of filling, a drill according to the invention can thus have an optimum geometry.

The drill according to the invention may have different shapes; it may e.g. be provided with a cylindrical or tapering cutting portion or with a cylindrical or tapering shaft. For instance, cemented carbide, stainless steel or tool steel may be used as the material for a dental drill according to the present invention.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Figure 1:
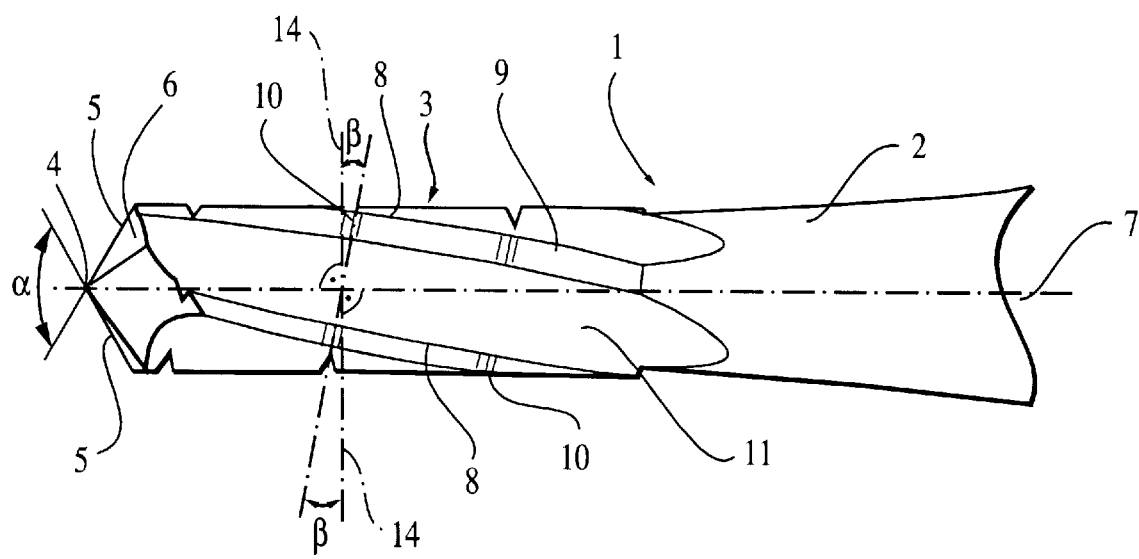
FIG. 1 is a lateral view of a dental drill of the invention according to a first embodiment of the present invention.
Figure 2:
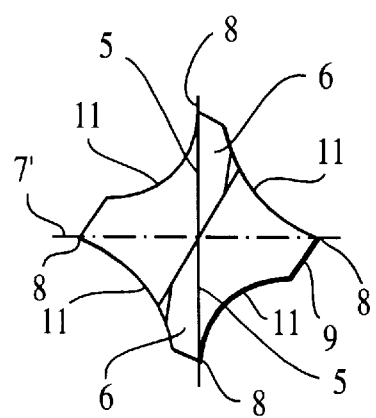
FIG. 2 is a front view of the dental drill shown in FIG. 1.

FIGS. 1 and 2 show a first embodiment of a dental drill 1 according to the invention. The dental drill 1 of this embodiment comprises a tapering shaft 2 and a cutting portion or head 3. The shaft 2 can be coupled to a drive means (not shown) so that the dental drill can be rotated. The cutting portion 3 comprises a hybrid toothing which consists of front and lateral cutting edges. The front side of the cutting portion 3 has two main cutting edges 5 and a transitional cutting edge, which form a tip 4. The tip 4 is located along a longitudinal central axis 7 in a central plane 7' of the dental drill 1. The tip 4 has an angle $\alpha$ of about 118° formed between cutting edges 5. Other acute angles are however also possible. For example, the angle $\alpha$ is preferably between approximately 110° and approximately 125°. The dental drill 1 has a symmetrical structure and comprises two further main flanks 6, which are each directly adjacent to the main cutting edges 5.

As best seen in FIG. 2, four lateral or secondary cutting edges 8 are provided in the lateral area of the dental drill 1. The lateral cutting edges 8 extend in helical fashion from the front part of the cutting portion 3 to the shaft 2. To increase the strength of the lateral cutting edges 8, a bevel 9 is arranged to adjoin each of the lateral cutting edges 8. Each of the lateral cutting edges 8 and each of the bevels 9, respectively, comprise incisions 10, which extend over the entire widths of the bevel 9. In this embodiment, the incisions 10 have a notched V-shaped form, but they may also have any other desired form, e.g. a U-shaped form or a polygonal form. Preferably, each of the lateral cutting edges 8 has provided thereon three incisions 10 that are respectively spaced apart from one another at the same distance. However, a different number of lateral cutting edges 8 or incisions 10 is also possible.

The incisions 10 are arranged at an angle $\beta$ relative to a line 14, which is perpendicular to the center axis 7 (cf. FIG. 1). The angle $\beta$ is preferably between 5° and 15°. In this embodiment, the respectively first or second or third incisions 10 of the individual lateral cutting edges 8 are located along a straight line (cf. FIG. 1), whereby the incisions 10 are respectively offset in the longitudinal direction of the dental drill. This additionally reduces the amount of heat generated during drilling because the lateral cutting edges 8 each contact different points of the filling. It is also possible that the incisions 10 are each arranged at different angles relative to the line 14 which is perpendicular to the center axis 7.

Moreover, four helical grooves or flutes 11 that are respectively arranged between the lateral cutting edges 8 are provided on the lateral area of the cutting portion 3. The helical grooves 11 are shaped in the form of a circular arc. Each of the helical grooves connect a first lateral cutting edge 8 to the bevel 9 of a second lateral cutting edge 8. The helical grooves 11 may also have a different geometrical design and the inclination of the grooves 11, in particular, can also have a different configuration.

Thus, the design of the cutting edges of the first embodiment with two main cutting edges 5 and four lateral cutting edges 8 have excellent performance during drilling in the axial direction, i.e. in the direction of the central axis 7. Moreover, these cutting edges 5 and 8 divide the drilled filling material, in particular amalgam, into relatively large pieces, so that the filling pieces can simply be sucked off from a patient's mouth, e.g. by means of a sucking device. Thanks to the cutting edges 8 that are laterally provided on the cutting portion 3, it is also possible to remove the filling by lateral contact. As a result of the incisions 10 that are provided at the lateral cutting edges 8, the frictional heat being generated is small. Therefore, mercury vapors are only observed to a very small extent. As a result, the mercury load, in particular on patients while amalgam fillings are being drilled out, can be reduced to a minimum. Since a dentist can drill out the filling also by lateral contact, the treatment time for drilling fillings is also reduced in comparison with the prior art. Hence, the dental drill according to the invention in the combination of main cutting edges 5 and lateral cutting edges 8 permits a rapid treatment that is not dangerous for the health of the patient and the dentist. Since the filling can also be drilled out by lateral contact, damage to and removal of healthy tooth material by the inventive dental drill during drilling are as small as possible.

Figure 3:
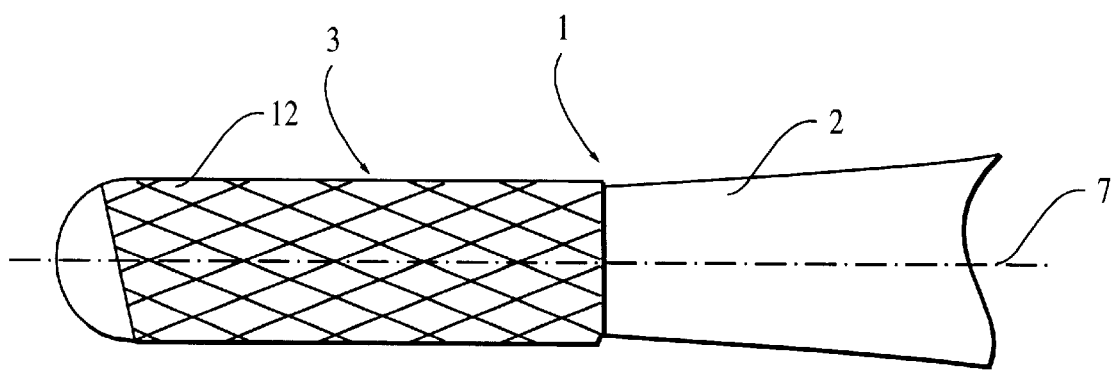
FIG. 3 is a schematic lateral view of a dental drill of the invention according to a second embodiment of the present invention.
Figure 4:
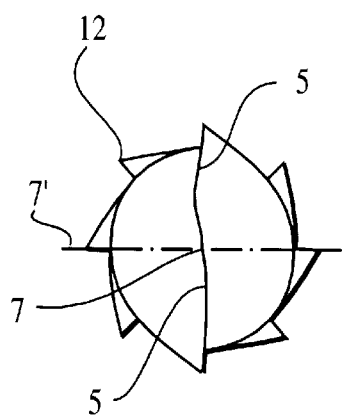
FIG. 4 is a front view of the dental drill shown in FIG. 3.

FIGS. 3 and 4 show a second embodiment of a dental drill 1 according to the invention. The dental drill 1 consists of a shaft 2 and a cutting portion 3. At its front end the cutting portion 3 comprises two main cutting edges 5 which form a transitional cutting edge of semicircular shape when viewed from the side (cf. FIG. 3). The two main cutting edges 5 converge at a central axis 7 in a symmetrical plane 7' of the dental drill (cf. FIG. 4). The transitional cutting edge has a curved shape and passes on the circumference of the drill into two lateral cutting edges 12. In this embodiment, the lateral cutting edges 12 are designed as a staggered or diamond toothing 12, with the lateral cutting edges dividing the lateral area of the cutting portion 3 into a plurality of rhombi or parallelograms.

The drill of the second embodiment of the invention also has a symmetrical structure and may be pointed in the front area of the cutting portion 3 at the transitional cutting edge 5. FIG. 3 is just a schematic view of the front area of the cutting portion 3. Furthermore, the cutting portion 3 has a cylindrical shape in this embodiment, but it may also have a conical or tapering shape.

Thanks to the provision of the diamond toothing 12 on the lateral area of the cutting portion 3 in combination with the main cutting edges 5 arranged at the front side, a dentist is capable of drilling filings axially and of removing filling material by lateral contact with the help of the diamond toothing 12. Since the cutting edges of the lateral cutting edges or diamond toothing 12 intersect or cross at the lateral area of the cutting portion 3, there are many free spaces between the individual cutting edges of the diamond toothing 12, so that the amount of heat developed during drilling of the filling is relatively small. Hence, the lateral edges or diamond toothing 12 also has the effect that mercury vapors are only produced to a small extent in the case of lateral contact drilling of the filling and that the filling material is divided into relatively large pieces which can then easily be removed from a patient's mouth. As a result, the mercury load on the patient in the case of amalgam fillings is minimized. The dental drill according to the invention also permits a considerable reduction of the treatment time in comparison with a drill according to the prior art. Moreover, thanks to the possibility of lateral contact drilling, the damage to or removal of healthy tooth material of a patient is as small as possible and mouth portions that are difficult to reach can be drilled rapidly and easily. Moreover, the surfaces achieved are of benefit to a subsequent treatment with plastic filling material.

Figure 5:
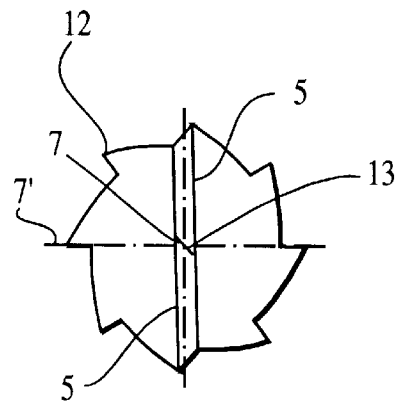
FIG. 5 is a front view of a dental drill of the invention according to a third embodiment of the present invention.

FIG. 5 is a front view of a dental drill according to a third embodiment of the present invention. Two main cutting edges 5 that are of a straight configuration are provided at the front side. The two main cutting edges 5 are interconnected via a transverse cutting edge 13. The transverse cutting edge 13 extends through a central axis 7 (longitudinal axis) which is perpendicular to the plane of projection (cf. FIG. 5). On the circumference of the dental drill the two main cutting edges 5 directly pass into two lateral cutting edges of a staggered or diamond toothing 12 (cf. FIG. 5). Both of the main cutting edges 5 extend along a circular path, which slightly projects beyond a central plane 7'. When viewed in a lateral direction, the main cutting edges form a semicircle, as shown, for example, in FIG. 3. The further structure of the dental drill shown in FIG. 5 corresponds to the second embodiment shown in FIG. 3, so that reference is made to the description thereof to avoid repetitions.

In summary, a dental drill with a shaft 2 and a cutting portion 3 provided with cutting edges 5 and 8 or 12 has been described. At the front side the dental drill 1 comprises two main cutting edges 5 and, laterally on the cutting portion, a plurality of additional cutting edges 8 or 12. The main cutting edges 5 converge in a central axis of the dental drill and directly pass into two lateral cutting edges 8 or 12.

While only three embodiments have been chosen to illustrate the present invention, it will be apparent to those skilled in the art from this disclosure that various changes and modifications can be made herein without departing from the scope of the invention as defined in the appended claims. Furthermore, the foregoing description of the embodiments according to the present invention are provided for illustration only, and not for the purpose of limiting the invention as defined by the appended claims and their equivalents.

What is claimed is:

1. A dental drill comprising
a shaft with a cutting end;
a cutting portion formed at said cutting end of said shaft and provided with two lateral cutting edges;
two main cutting edges provided at a front side of said cutting portion, said main cutting edges converging toward a central axis of said shaft and radially extending directly into said lateral cutting edges; and
at least two additional lateral cutting edges provided on said cutting portion such that said additional lateral cutting edges do not extend directly into cutting edges formed at said front side of said cutting portion, said lateral cutting edges and said additional lateral cutting edges being arranged along helical lines and configured as staggered toothing.

2. The dental drill according to claim 1, wherein said main cutting edges meet to form a tip of said cutting portion.

3. The dental drill according to claim 2, wherein said main cutting edges meet to form a semicircle when viewed laterally.

4. The dental drill according to claim 1, wherein said main cutting edges meet to form a semicircle when viewed laterally.

5. The dental drill according to claim 1, wherein said main cutting edges are straight edges that are parallel to one another.

6. The dental drill according to claim 2, wherein said main cutting edges are curved edges.

7. The dental drill according to claim 1, wherein said main cutting edges are curved edges.

8. The dental drill according to claim 1, wherein said cutting portion is a cylindrical member.

9. The dental drill according to claim 1, wherein said cutting portion is a tapered member.

* * * * *